United States Patent [19]

Lewalter et al.

[11] 4,289,868

[45] Sep. 15, 1981

[54] POLYHYDANTOINS FROM UNSATURATED CARBOXYLIC ACIDS AND POLYISO(THIO)CYANATES

[75] Inventors: Jürgen Lewalter, Odenthal; Rudolf Merten, Leverkusen; Wilfried Zecher, Leverkusen; Willi Dünwald, Leverkusen, all of Fed. Rep. of Germany

[73] Assignee: Bayer Aktiengesellschaft, Leverkusen, Fed. Rep. of Germany

[21] Appl. No.: 100,712

[22] Filed: Dec. 6, 1979

Related U.S. Application Data

[63] Continuation of Ser. No. 958,940, Nov. 8, 1978, abandoned.

[51] Int. Cl.³ .................... C08G 18/34; C08G 18/38; C08G 18/67; C07D 233/80
[52] U.S. Cl. ..................... 528/73; 528/45; 528/48; 528/49; 528/52; 528/53; 528/54; 528/55; 528/56; 528/58; 528/75; 548/308; 548/310; 548/317; 548/319
[58] Field of Search .................... 528/75, 73

[56] References Cited

U.S. PATENT DOCUMENTS

| | | | |
|---|---|---|---|
| 3,549,599 | 12/1970 | Merten .................. | 528/73 |
| 4,089,860 | 5/1978 | Merten et al. .......... | 233/78 |
| 4,182,812 | 1/1980 | Zecher et al. .......... | 528/73 |
| 4,196,274 | 4/1980 | Zecher et al. .......... | 528/73 |

FOREIGN PATENT DOCUMENTS 1186829 4/1970 United Kingdom ............... 548/310

*Primary Examiner*—H. S. Cockeram
*Attorney, Agent, or Firm*—Connolly and Hutz

[57] ABSTRACT

Poly(thio)hydantoins are prepared by reacting an iso(thio)cyanate having at least two iso(thio)cyanate moieties with a compound of the formula

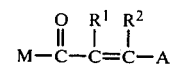

wherein $R^1$ and $R^2$ are the same or different and each represents hydrogen, halogen, a $C_1$–$C_{20}$ aliphatic group, a $C_7$–$C_{20}$ aliphatic-aromatic group, a $C_6$–$C_{20}$ aromatic group or a heterocyclic group having from 4 to 16 ring members and at least one N, O or S atom;

A represents CN, COR, substituted or unsubstituted $C_1$–$C_{20}$ aliphatic group, $C_7$–$C_{20}$ aliphatic-aromatic group, $C_6$–$C_{20}$ aromatic group or a heterocyclic group having from 4 to 16 ring members and at least one N, O or S atom wherein the substituents are $NO_2$, $COOR_4$, CN, CO or OH; R and $R^4$ are selected from the definition of $R^1$ and $R^2$ with the exclusion of halogen;

M represents OH or

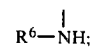

and $R^6$ represents hydrogen, unsubstituted or substituted $C_2$–$C_{20}$ aliphatic, $C_5$–$C_{12}$ cycloaliphatic, $C_6$–$C_{20}$ aliphatic aromatic, or a $C_5$–$C_{12}$ aromatic or $C_5$–$C_{12}$ cycloaliphatic containing a heteroatom N, O or S in the ring, wherein the substituents are at least one halogen, $C_1$–$C_{10}$ alkyl, or $C_6$–$C_{12}$ aryl.

3 Claims, No Drawings

POLYHYDANTOINS FROM UNSATURATED CARBOXYLIC ACIDS AND POLYISO(THIO)CYANATES

This is a continuation of Ser. No. 958,940, filed Nov. 8, 1978, now abandoned.

This invention relates to condensates having at least one hydantoin or thiohydantoin ring in the molecule, to the preparation thereof by reacting unsaturated carboxylic acids respectively acid derivatives with organic isocyanates and to the use thereof as biochemically active substances or for the production of heat-resistant coating compounds.

Processes for the preparation of hydantoins (J. Am. Chem. 45/383) and polyhydantoins (Belgian Pat. No. 678,282) are known. Low molecular weight hydantoins are mainly used in the pharmaceutical field and in the plant protective agents, while higher molecular weight hydantoins are used, for example, in heat-resistant coating compounds (French Pat. No. 1,484,694).

It has now surprisingly been found that by reacting organic iso(thio)cyanates with unsaturated carboxylic acid derivatives corresponding to the following general formula I:

$$Y-\overset{O}{\underset{\|}{C}}-\overset{R^1}{\underset{|}{C}}=\overset{R^2}{\underset{|}{C}}-A, \qquad (I)$$

Wherein
  $R_1$ and $R_2$, which may be the same or different, each represents hydrogen, halogen or a substituted or unsubstituted aliphatic, aliphatic-aromatic, aromatic or heterocyclic group;
  A represents CN, COR (wherein R represents hydrogen or an aliphatic, aliphatic-aromatic, aromatic or hetrocyclic group) or a substituted or unsubstituted aromatic, aliphatic, aliphatic-aromatic or heterocyclic group; and
  Y represents OH or $R^6$—NH (wherein $R^6$ represents hydrogen or $R^5$);

at temperatures of from $-20°$ to $+500°$ C., (thio)hydantoins of the x-times recurring structural units IIa and IIb are obtained:

$$\text{(IIa)}$$

$$\text{(IIb)}$$

wherein
  $R^1$, $R^2$, $R^6$ and A are as defined above; and
  $R^5$ represents a substituted or unsubstituted, aliphatic, aliphatic-aromatic, aromatic or heterocyclic group; and
  O represents O or S,
  x represents an integer of from 1 to 1000, preferably from 1 to 200.

The process according to the present invention may be represented by the following equations wherein the various substituents are as defined in connection with formulae (IIa/b):

$$HO-\overset{O}{\underset{\|}{C}}-\overset{R^1}{\underset{|}{C}}=\overset{R^2}{\underset{|}{C}}-A + z \cdot R_5\text{+}NCO)_n \longrightarrow \qquad (Ia)$$

$$\text{(IIa)}$$

$$R^6\text{+}NH-\overset{O}{\underset{\|}{C}}-\overset{R^1}{\underset{|}{C}}=\overset{R^2}{\underset{|}{C}}-A\Big)_m + (Z-1) R^5\text{+}NCO)_n \longrightarrow \qquad (Ib)$$

$$\text{(IIb)}$$

wherein
  z is 1 to 2; Monomolecular compounds may be formed when
  n and m each represents 1 and higher molecular weight compounds may be formed when
  n and m each $>1$ the hydantoin rings of the compounds being linked via $R^6$ and/or $R^5$. In these compounds the hydantoin rings may be linked through 1-,3- or through 3-,1- or through all the possible linkages in statistical sequence.

The present invention therefore also relates to monomolecular hydantoins corresponding to the following general formula (III):

$$\text{(III)}$$

with $R^7=R^6$ and/or $R^5$; higher molecular hydantoins corresponding to the formula (IIa) or (IIb) and polyisocyanates corresponding to the following general formulae (IV):

$$\text{(IVa)}$$

$$\text{(IVb)}$$

wherein A, $R^1$, $R^2$, $R^5$ and $R^6$ are as defined above; and p represents an integer of from 1 to 100.

The hydantoins according to the present invention may be identified by the characteristic IR bands of the hydantoins. As 30%, by weight, solutions in acetophenone, butyrolactone, caprolactone or methyl benzoate, the higher molecular weight hydantoins have solution viscosities at 20° C. of from 200 to 200,000 mPas, preferably from 500 to 50,000 mPas.

The unsaturated carboxylic acids used as starting materials according to the present invention wherein Y represents OH are compounds corresponding to the following general formula (Ia)

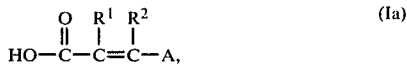

wherein $R^1$, $R^2$ and A preferably have the following meaning:
$R^1$ and $R^2$, which may be the same or different, each represents hydrogen, halogen, a $C_1$-$C_{20}$ aliphatic group, a $C_7$-$C_{20}$ aliphatic-aromatic group, a $C_6$-$C_{20}$ aromatic group or a heterocyclic group having from 4 to 16 ring members and at least one N, O or S atom; and A represents a $C_1$-$C_{20}$ aliphatic group, a $C_7$-$C_{20}$ aliphatic-aromatic group, a $C_6$-$C_{20}$ aromatic group or a heterocyclic group having from 4 to 16 ring members which may be substituted by halogen (chlorine, bromine), $NO_2$, $COOR_4$, CN, CO or OH, (wherein $R_4=R_1$ with the exclusion of halogen); CN or COR (wherein R represents hydrogen, a $C_1$-$C_{20}$ aliphatic group, a $C_7$-$C_{20}$ aliphatic-aromatic group, a $C_6$-$C_{20}$ aromatic or a heterocyclic group having from 4 to 16 ring members and at least one N, O or S atom).

$R^1$ and $R^2$ may be preferably hydrogen, fluorine chlorine, bromine or a methane, ethane, hexane, cyclohexane, propene, benzene, toluene, piperidine, morpholine or imidazole group and they may combine to form a ring having up to 8 ring members.

The group represented by A is preferably a CN-group, an acetyl, benzoyl, benzene, naphthalene or oxazoline group and it may combine with $R^2$ to form a ring having up to 8 ring members.

$R^1$ and $R^2$ are most preferably hydrogen and A is most preferably a phenyl group.

The unsaturated carboxylic acid amides used as starting materials according to the present invention wherein m represents $R^6$—NH correspond to the following general formula (Ib):

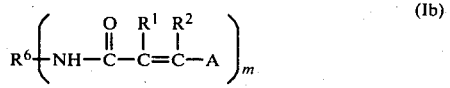

wherein $R^1$, $R^2$ and A are as defined above and $R^6$ has the definition of $R^5$ and m is 1 or 2 may be prepared in situ from the unsaturated carboxylic acids (Ia) and organic isocyanates or they may be prepared by a separate, known reaction for example from unsaturated carboxylic acids (Ia) and organic isocyanates, unsaturated carboxylic acid esters and the amines corresponding to these isocyanates.

The organic isocyanates used may be mono- and/or poly-isocyanates.

The monoisocyanates used for the inventive process may be aliphatic or aromatic compounds having an isocyanate group in the molecule and optionally substituted by heteroatoms, e.g. alkyl isocyanates, such as ethyl, methyl, butyl, dodecyl or stearyl isocyanate, aromatic substituted or unsubstituted monoisocyanates, such as phenyl, tolyl, isopropyl or nonyl isocyanate, nitro, alkoxy, aroxy, chloro, dichloro, trichloro, tetrachloro, pentachloro, benzyl or bomophenyl isocyanate or isocyanato-benzoic acid esters, -phthalic acid esters or -isophthalic acid esters, isocyanato benzonitrile, cycloaliphatic isocyanates, such as cyclohexyl isocyanate, or unsaturated isocyanates, such as allyl, oleyl or cyclohexenyl isocyanate.

Aliphatic, cycloaliphatic, araliphatic, aromatic and heterocyclic polyisocyanates (see Annalen 562, pages 75 to 136) may also be used as starting components according to the present invention, for example ethylene diisocyanate; 1,4-tetramethylene diisocyanate; 1,6-hexamethylene diisocyanate; 1,12-dodecane diisocyanate; cyclobutane-1,3-diisocyanate; cyclohexane-1,3- and 1,4-diisocyanate and mixtures of these isomers; 1-isocyanato-3,3,5-trimethyl-5-isocyanato methyl-cyclohexane (German Auslegeschrift No. 1,202,785); 2,4- and 2,6-hexahydrotolylene diisocyanate and mixtures of these isomers; hexahydro-1,3- and/or 1,4-phenylene diisocyanate; perhydro-2,4'- and/or 4,4'-diphenyl methane-diisocyanate; 1,3- and 1,4-phenylene diisocyanate; 2,4- and 2,6-tolylene diisocyanate and mixtures of these isomers; diphenyl methane-2,4'- and/or 4,4'-diisocyanate; naphthylene-1,5-diisocyanate; triphenyl methane-4,4',4''-triisocyanate; polyphenyl-polymethylene polyisocyanates which may be obtained by aniline/formaldehyde condensation, followed by phosgenation, e.g. those described in British Pat. Nos. 874,430 and 848,671; perchlorinated aryl polyisocyanates, e.g. those described in German Auslegeschrift No. 1,157,601; polyisocyanates containing carbodiimide groups as described in German Pat. No. 1,092,007; the diisocyanates described in U.S. Pat. No. 3,492,330; polyisocyanates containing allophanate groups as described, e.g. in British Pat. No. 994,890, Belgian Pat. No. 761,626 and published Dutch Patent Application No. 7,102,524; polyisocyanates containing isocyanurate groups as described, e.g. in German Pat. Nos. 1,022,789; 1,222,067 and 1,027,394 and in German Offlenegungsschrift Nos. 1,929,034 and 2,004,048; polyisocyanates containing urethane groups as described, e.g. in Belgian Pat. No. 752,261 or in U.S. Pat. No. 3,394,164; polyisocyanates containing acylated urea groups according to German Pat. No. 1,230,778, polyisocyanates containing biuret groups as described, e.g. in German Pat. No. 1,101,394, British Pat. No. 889,050 and French Pat. No. 7,017,514, polyisocyanates prepared by telomerisation reactions, e.g. as described in Belgian Pat. No. 723,640; polyisocyanates containing ester groups, e.g. as described in British Pat. Nos. 956,474, and 1,072,956, U.S. Pat. No. 3,567,763 and German Pat. No. 1,231,688; and reaction products of the above-mentioned isocyanates with acetals according to German Pat. No. 1,072,358.

The distillation residues containing isocyanate groups from the commercial production of isocyanates may also be used, optionally dissolved in one or more of the above-mentioned polyisocyanates. Mixtures of the above-mentioned polyisocyanates may also be used.

Particularly suitable isocyanates are those corresponding to the following general formula (V)

$$R^5(-NCO)_n \tag{V}$$

wherein $R^5$ represents a $C_2$-$C_{20}$ alkyl group; a $C_5$-$C_{12}$ cycloalkyl group; a $C_6$-$C_{20}$ alkaryl group or a $C_5$-$C_{12}$ aryl or $C_5$–$C_{12}$ cycloalkyl group containing heteroatoms such as N, O or S in the ring which all may be substituted by halogen, by $C_1$–$C_{10}$ alkyl groups and/or by $C_6$–$C_{12}$ aryl groups. In the above general formula, n represents an integer of from 1 to 4, preferably from 1 to 3, most preferably 2. Aliphatic groups having from 2 to 12 carbon atoms or aryl groups, such as phenyl, tolyl, naphthyl diphenyl methane and diphenyl ether groups are particularly preferred.

It is preferred to use commercially readily available mixtures of tolylene diisocyanates, m-phenylene diisocyanate and phosgenated condensates of aniline and formaldehyde which have a polyphenylene-methylene structure and the symmetric compounds, 4,4'-diisocyanato diphenyl methane, 4,4'-diisocyanato diphenyl ether, p-phenylene diisocyanate and 4,4'-diisocyanato diphenyl dimethyl methane, as well as isophorone diisocyanate and hexamethylene diisocyanate.

The isocyanates may be used in the free form or partly or completely in the form of derivatives which are obtained by reacting the isocyanates with compounds containing isocyanate reactive hydrogen and which function as isocyanate-releasing compounds under the reaction conditions.

The isocyanate-releasing compounds used are preferably addition products of lactams, oximes and CH-acidic compounds, as well as the carbamic acid esters obtained from aliphatic and aromatic mono- and polyhydroxyl compounds, for example those corresponding to the following general formulae:

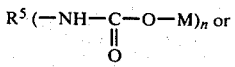

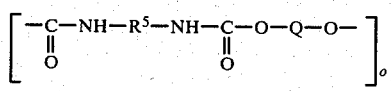

wherein $R^5$ and n are as defined above; M represents the organic group of a monohydroxy compound; and Q represents the organic group of a difunctional or trifunctional hydroxy compound. M and Q, which may be the same or different, preferably represent a $C_1$–$C_{10}$ aliphatic group, a $C_5$–$C_{10}$ cycloaliphatic group, a $C_7$–$C_{12}$ aliphatic-aromatic group or a $C_6$–$C_{12}$ aromatic group, each of which may be substituted by $C_1$–$C_{10}$ alkyl groups and/or $C_6$–$C_{12}$ aryl groups; and o represents an integer of from 1 to 1000, preferably from 1 to 100.

Examples include: the carbamic acid esters of phenol the isomeric cresols, commercial mixtures thereof, aliphatic monohydric alcohols, such as methanol, ethanol, propanol, isopropanol, butanol, isobutanol, cyclohexanol and allyl alcohol, benzyl alcohol and aliphatic diols or polyols, such as ethylene glycol and trimethylol propane; also addition products with pyrrolidone-(2), caprolactam, butanone oxime, malonic acid esters, ethyl acetoacetate and aceto phenone.

The isocyanate-releasing compounds may be put into the process as previously prepared compounds or they may be produced in situ by reaction with the appropriate reactants.

Instead of the above-mentioned (poly)isocyanates, the analogous (poly)isothiocyanates may be used as starting materials.

The hydroxy alkyl ethers which are particularly preferred both as blocking agents and as solvents according to the present invention include, for example, compounds corresponding to the following general formula (VI):

wherein $R^8$ represents a substituted or unsubstituted $C_1$–$C_{20}$, preferably $C_1$–$C_8$, aliphatic group, $C_3$–$C_{10}$, preferably $C_4$–$C_8$, cycloaliphatic group, $C_7$–$C_{16}$ aliphatic-aromatic group or $C_6$–$C_{14}$ aromatic group, which group may by substituted one or more times by e.g. alkoxy, aroxy or hydroxyl; $R^9$ represents a $C_2$–$C_{20}$ aliphatic group; and q represents an integer of from 1 to 100, preferably from 1 to 4. The hydroxy alkyl ethers used according to the present invention are preferably those which contain one hydroxyl group per molecule and wherein $R^9$ represents a group having two carbon atoms in the chain which may be substituted one or more times e.g. by alkyl groups, e.g. methyl, isopropyl, cyclohexyl, benzyl or phenyl monoethers or methoxy ethylethylene glycol or -propylene glycol or -diethylene glycol or -dipropylene glycol monoethers.

The reaction according to the present invention of unsaturated carboxylic acids corresponding to general formula (Ia) or carboxylic acid amides corresponding to general formula (Ib) with organic isocyanates to produce the hydantoins or hydantoin group-containing polyiso(thio) cyanates according to the present invention may be carried out in solvents which are either inert under the reaction conditions or form loose addition compounds which undergo further reaction, or it may be carried out in an excess of one of the reactants.

Apart from the above-mentioned blocking agents, the following are also suitable solvents: hydrocarbons, halogenated hydrocarbons, phenols, esters, cyclic esters, ketones, ethers, substituted amides and nitriles; for example, xylenes, o-dichlorobenzene, phenol, cresols, acetophenone, cyclohexanone, ε-caprolactam, ethylene glycol butyl ether, diethylene glycol methyl ether, glycol monomethyl ether acetate, γ-butyrolactone, ε-caprolactone, benzoic acid alkyl esters, N-methyl pyrrolidone, dimethyl formamide, dimethyl acetamide, benzonitrile and others and mixtures thereof. It is preferred, however, to use no solvents or only stoichiometric quantities of blocking agents.

To carry out the process according to the present invention, the reactants, optionally with, but preferably without, solvent, are maintained at temperatures of from $-20°$ to $+500°$ C., preferably from $0°$ to $450°$ C., for periods of from several minutes to several hours, optionally in the presence of blocking agents. The progress of the reaction may be followed by the evolution of gas and the IR spectra.

The high velocity of the reaction according to the present invention enables it to be carried out in the presence of phenolic and/or alcoholic hydroxyl groups and/or lactonic amide groups, so that such groups may be present in the reaction components, optionally as blocking agents, and excess hydroxyl or lactam components may also be used as solvents.

the acidity of acid in solvents, such as phenols or cresols, in sufficient for carrying out the reaction within sufficiently short reaction times. In inert media or in solvent-free reaction mixtures, it is possible, for example, to use carboxylic acids having sufficiently high melting or boiling points, such as acetic acid, benzoic acid, succinic acid, benzodicarboxylic acids, butane tetracarboxylic acid, trimellitic acid or the anhydrides thereof, optionally as catalysts which may be chemically incorporated. They may be used in quantities of from 0.1 to 40, preferably from 1 to 10, percent by Val, based on one Val of isocyanate.

The reactions may be further accelerated by the bases, acids and/or metal catalysts known in isocyanate chemistry, such as trimethylamine, N-methyl morpholine, endoethylene piperazine, titanium tetrabutylate, titanium amino alcohol, iron acetyl acetonate, dibutyl tin laurate or p-toluene sulphonic acid.

It is sometimes advantageous to carry out the reactions in several stages or to add the individual components in a different sequence, possibly also at different temperatures. Thus, for example, an adduct or condensate may be prepared in a first stage, optionally in a solvent and/or blocking agent, and this may then be converted into an optionally high molecular weight condensation product by a process of ring-closure and/or chain-lengthening and/or cross-linking at a higher temperature, optionally with evaporation of the solvent and optionally after the addition of latent blocking agents. If such a condensation product is to be used as a coating, it may be applied from solvent-free melts or from aqueous systems.

It is sometimes desirable to carry out the reaction under an inert gas, such as $N_2$ or argon.

Lastly, the reaction according to the present invention may be carried out either continuously or batchwise, optionally in autoclaves under pressure in order to obtain a higher reaction temperature.

In general, depending on the particular reaction according to the present invention, at least one equivalent of isocyanate is advantageously used per functional COOH-group, as well as per CONH-group which may be produced separately or formed as part of an intermediate product.

However, the process according to the present invention may also be carried out using a proportion of NCO groups to functional COOH-groups and/or CONH-groups within a range of molar ratios of from $\geq 2:1$ to 1:1. Very wide deviations from this molar ratio may be employed in order to adapt the properties of the polyisocyanates prepared according to the present invention to various forms of application although it is only useful to employ molar ratios which give rise to products which are at least fusible and/or soluble in organic solvents.

According to another embodiment of the inventive process, isocyanate mixtures may be used, so that other organic isocyanates may be used, for example for amide or hydantoin ring formation.

When reacted with monofunctional isocyanates, the unsaturated carboxylic acids corresponding to general formula (Ia) and corresponding carboxylic acid amides corresponding to general formula (Ib) give rise to monomolecular hydantoins, whereas when reacted with diisocyanates they give rise to relatively high molecular or very high molecular, in part cross-linked polyhydantoins, depending on the stoichiometric proportions, and in some cases also to polyisocyanates containing oligomeric and monomeric hydantoin groups.

Products containing masked isocyanate groups may be obtained by the process according to the present invention.

Compounds having a comparable degree of polymerisation, but containing a lower proportion of isocyanate groups (which may be masked) may be obtained by the addition of calculated proportions of monoisocyanates. Suitable monoisocyanates for this purpose are, for example, phenyl isocyanate, α-naphthyl isocyanate, isocyanato benzoic acid esters and isocyanato acetic acid esters.

The hydantoins obtained, which may be modified or substituted with isocyanate or carbamic acid derivatives or with carboxylic acid ester, -amide or -amido urethane groups, and which may in part be realtively high molecular products, may be worked-up by the conventional methods, such as crystallisation, but this is, in most cases, unnecessary because these products, optionally in a completely condensed form and optionally in statu nascendi and optionally after conversion of the acid and/or alcohol functions thereof, optionally by combination with optionally polyfunctional amines, optionally polyhydric alcohols, such as ethylene glycol, trimethylol propane or glycerol, tris-hydroxy ethylisocyanurate and/or optionally polybasic carboxylic acids or anhydrides thereof, such as phthalic acid, isophthalic acid, terephthalic acid, trimellitic acid or butane tetracarboxylic acid, and optionally with the addition of other polyisocyanates or polyisocyanate-releasing compounds, may be converted by the conventional reactions into linear and/or branched chain synthetic materials which have good solubility, relatively high temperature resistance, high elasticity and high heat-shock resistance.

The condensation products according to the present invention and optionally also the preliminary stages thereof may be added with similar success to polyesters of phthalic acid-terephthalic acid/isophthalic acid or esters thereof, ethylene glycol, glycerol/trimethylol propane/tris-hydroxy ethylisocyanurate, polyethers of ethylene oxide and/or bis-(hydroxy phenyl)-propane and epichlorohydrin, polyurethanes or polyamides, and may be chemically added by condensation and/or incorporated by condensation. In all cases, the products obtained are then modified polymers which, in addition to (thio)hydantoin rings, may contain additional ether, -carbamic acid derivative, -carboxylic acid esters, -amide, -imide, -ester amide, -ester imide, -amido imide and/or -ester amido imide groups.

The quantitative proportions of these additives may vary within wide ranges, but are preferably used in quantities of from 10 to 400%, by weight, based on the condensate according to the present invention.

The low molecular weight or monomolecular hydantoins obtainable by the process according to the present invention have biochemical actions while the polyhydantoins according to the present invention have exceptional temperature resistance.

Polymers which have been modified by the polycondensates according to the present invention manifest improved temperature characteristics, as well as universal solubility. The polymers may be used for the manufacture of temperature-resistant adhesives, lacquers, powders, foils and synthetic resins, as well as for the coating of heat-resistant substrates. The characteristics thereof may be varied within wide limits by the addition of fillers, pigments and low and high molecular weight components according to the fields in which they are to be used.

EXAMPLE 1

307.1 g of 4-chlorophenyl isocyanate are first mixed at room temperature with
410 g of γ-butyrolactone and 4.6 g of o-dichlorobenzene under an atmosphere of nitrogen and then, upwards of a temperature of from 10° to 30° C., as CO₂ evolves, the reactants are mixed with 148.2 g of cinnamic acid and then stirred for 1 hour at 50° C.

0.5 g of Endoethylenepiperazin is added and the mixture is then stirred at temperatures of 70°/100°/120°/150°/175° C. and finally under reflux until evolution of CO₂ ceases and all the isocyanate groups have been used up.

The product is worked-up by distilling the solvent under vacuum and recrystallising the residue from ethanol/petroleum ether.

Almost colourless to pale yellow crystals melting at 178°–180° C. are obtained. The IR spectrum thereof shows the typical bands of hydantoins at 1710 and 1755 cm$^{-1}$. The analytical results for 1,3-bis-(4-chlorophenyl)-5- benzyl hydantoin, calculated on the basis of $C_{22}H_{16}N_2O_2Cl_2$ (411.3) are as follows:

calculated: C 64.2, H 3.9, N 6.8, Cl 17.2: observed: C 64.5, H 4.0, N 6.6, Cl 16.7.

EXAMPLE 2

169 g of mucochloric acid are dissolved in 500 g of γ-butyrolactone at 25° C. under nitrogen. A solution of 250.2 g of 4,4'-diisocyanato diphenyl methane in 200 g of toluene is then added at from 30° to 50° C.

The reaction mixture continues to be stirred at 30° C. and then as evolution of gas takes place, it is heated at from 170° to 190° C. until the isocyanate test is negative. As the viscosity increases, the reaction mixture is diluted with X g of γ-butyrolactone and finally, at from 140° to 120° C., with a total of (375-X)g of γ-butyrolactone and finally stirred for about 1 hour at 200° C.

The viscosity of the resulting solution is 1730 cP₂₀° C. A deep drawn sheet metal coated with this lacquer solution and stoved at 250° C. for 15 minutes and at 300° C. for 10 minutes has an elastic, firmly adhereing lacquer film which has good surface hardness and excellent resistance to solvents.

EXAMPLE 3

296.3 g of cinnamic acid are dissolved in 500 g of γ-butyrolactone under nitrogen.

222.0 g of isophorone diisocyanate are then added at from 30 to ≦50° C. and the mixture is stirred at from 150° to 180° C. until the isocyanate test is negative.

250.2 g of 4,4'-diisocyanato diphenyl methane and 0.5 g of triethylene diamine are then added at 70° C. and the reaction mixture is finally heated to from 200° to 205° C. for 9 hours until all the isocyanate groups have been used up.

As the viscosity rises, the reaction mixture may be diluted, first with X g of acetophenone and then, at from 170° to 150° C., with (1588-X)g of methyl benzoate. After further stirring for 1 hour at 170° C., the lacquer solution has a viscosity of 1270 cP₂₀° C.

The binder left behind after methanol precipitation shows the characteristic hydantoin bands in the IR spectrum.

A lacquered 0.7 mm copper wire obtained by applying the above lacquer solution and passing through a 4 meter furnace at the rate of 9 meters per minute has a softening temperature above 330° C., a heat-shock temperature above 220° C. and a permanent heat endurance of at least 14 days at 180° C.

We claim:

1. A process for the preparation of polyhydantoins and polythiohydantoins, comprising reacting organic polyisocyanates or polyisothiocyanates at temperatures of from −20° to +500° C. with compounds consisting essentially of unsaturated carboxylic acid derivatives of the formula:

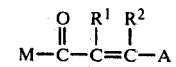

wherein $R^1$ and $R^2$ are the same or different and each represents hydrogen, halogen, a $C_1$–$C_{20}$ aliphatic group, a $C_7$–$C_{20}$ aliphatic-aromatic group, a $C_6$–$C_{20}$ aromatic group or a hetercyclic group having from 4 to 16 ring members and at least one N, O or S atom;

A represents CN, COR, substituted or unsubstituted $C_1$–$C_{20}$ aliphatic group, $C_7$–$C_{20}$ aliphatic-aromatic group, $C_6$–$C_{20}$ aromatic group or a heterocyclic group having from 4 to 16 ring members and at least one N, O or S atom wherein the substituents are $NO_2$, $COOR_4$, CN, CO or OH; R and $R^4$ are selected from the definition of $R^1$ and $R^2$ with the exclusion of halogen;

M represents OH or

and $R^6$ represents hydrogen, unsubstituted or substituted $C_2$–$C_{20}$ aliphatic, $C_5$–$C_{12}$ cycloaliphatic, $C_6$–$C_{20}$ aliphatic aromatic, or a $C_5$–$C_{12}$ aromatic or $C_5$–$C_{12}$ cycloaliphatic containing a heteroatom N, O or S in the ring, wherein the substituents are at least one halogen, $C_1$–$C_{10}$ alkyl or $C_6$–$C_{12}$ aryl.

2. A process as claimed in claim 1 wherein the unsaturated carboxylic acid derivative correspond to the formula

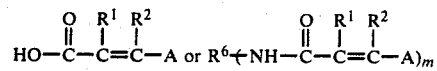

wherein $R^1$ and $R^2$, which may be the same or different, each represents hydrogen, halogen, a $C_1$–$C_{20}$ aliphatic group, a $C_7$–$C_{20}$ aliphatic-aromatic group, a $C_6$–$C_{20}$ aromatic group or a heterocyclic group having from 4 to 16 ring members and at least one N, O or S atom;

A represents a substituted or unsubstituted $C_1$–$C_{20}$ aliphatic group, a $C_7$–$C_{20}$ aliphatic-aromatic group, a $C_6$–$C_{20}$ aromatic group or a heterocyclic group having from 4 to 16 ring members and at least one N, O or S atom wherein the substituents of the substituted moieties are halogen, $NO_2$, $COOR_4$, CN, CO, OH, CN or COR wherein $R_4$ is the same as $R_1$ wherein R represents hydrogen, a $C_1$–$C_{20}$ aliphatic group, a $C_7$–$C_{20}$ aliphatic-aromatic group, a $C_6$–$C_{20}$ aromatic group or a heterocyclic group having from 4 to 16 ring members and at least one N, O or S atoms;

$R^6$ represents hydrogen, a $C_2$–$C_{20}$ aliphatic group, a $C_5$–$C_{12}$ cycloaliphatic group, a $C_6$–$C_{12}$ aliphatic-aromatic group, or a $C_5$–$C_{12}$ aromatic or $C_5$–$C_{12}$ cycloaliphatic group containing N, O or S heteroatoms in the ring, each of which may be substituted by halogen, by $C_1$–$C_{10}$ alkyl groups and/or by $C_6$–$C_{12}$ aryl groups and m is 1 or 2.

3. A process as claimed in claim 1, wherein as unsaturated carboxylic acid, cinnamic acid is used.

* * * * *